United States Patent [19]

Urban et al.

[11] Patent Number: 5,021,345
[45] Date of Patent: Jun. 4, 1991

[54] IMMOBILZATION OF LIPASE FOR RESOLVING RACEMATES OF ESTERS OF RACEMIC ALCOHOLS

[75] Inventors: Dieter Urban, Mannheim; Wolfgang Ladner, Fussgoenheim; Axel Paul, Mannheim, all of Fed. Rep. of Germany

[73] Assignee: BASF Aktiengesellschaft, Ludwigshafen, Fed. Rep. of Germany

[21] Appl. No.: 267,287

[22] Filed: Nov. 4, 1988

[30] Foreign Application Priority Data

Nov. 4, 1987 [DE] Fed. Rep. of Germany ....... 3737335

[51] Int. Cl.$^5$ ...................... C12N 11/08; C12N 9/20; C12P 7/62; C07C 67/00
[52] U.S. Cl. .................................... 435/180; 435/135; 435/182; 435/198; 435/280
[58] Field of Search .............. 435/174, 177, 180, 182, 435/198, 135, 155, 280

[56] References Cited

U.S. PATENT DOCUMENTS

| | | | |
|---|---|---|---|
| 4,451,582 | 5/1984 | Denzinger et al. | 435/188 X |
| 4,629,742 | 12/1986 | Brady et al. | 521/55 |
| 4,732,853 | 3/1988 | Whitesides et al. | 435/198 X |
| 4,767,707 | 8/1988 | Marcinowski et al. | 435/182 |
| 4,798,793 | 1/1989 | Eigtued | 435/180 X |
| 4,818,695 | 4/1989 | Eigtued | 435/180 X |

FOREIGN PATENT DOCUMENTS 0210499 2/1987 European Pat. Off.
0183691 10/1984 Japan .................................. 435/198

OTHER PUBLICATIONS

Applied Biochemistry & Microbiology, vol. 14, Nr. 5, Sep./Oct. 1978, "Immobilization . . . Epoxy Groups".
Journal of American Chemical Society 1984, 106, pp. 7250-7251 Lipase-Catalyzed Hydrolysis as a Route to Esters of chiral Epoxy Alcohols, Wolfgang Ladner, et al.

Primary Examiner—David M. Naff
Attorney, Agent, or Firm—Oblon, Spivak, McClelland, Maier & Neustadt

[57] ABSTRACT

Lipase is immobilized by mixing a substrate, a crude porcine pancreatic lipase, an aqueous buffer solution at pH 5-9 and one or more water-soluble polyhydric aliphatic alcohols having from 2 to 6 carbon atoms and from 2 to 6 hydroxyl groups at a temperature of from 0° to 40° C. to form a mixture, allowing the mixture to stand for from 1 minute to 3 days, filtering the mixture to produce a filter cake and washing the cake to obtain the immobilized lipase. The substrate is a pulverulent, insoluble, only slightly swellable copolymer of one or more N-vinyllactams of 4 to 6 carbon atoms with a cyclic amide which contains two or more ethylenically unsaturated, copolymerizable groups, one or more of which are bonded directly to amide nitrogen. The polyhydric aliphatic alcohol can be combined with one or more water-soluble monohydric alcohols having from 1 to 4 carbon atoms. The filter cake can be treated with a crosslinking agent such as a water-soluble glycidyl ether which is prepared by reacting an epoxide with a polyfunctional alcohol to form an adduct and reacting the adduct with epichlorohydrin followed by cyclization to give an epoxide. The immobilized lipase is used for resolving a racemate of an ester of a racemic alcohol such as a racemate of glycidyl butyrate.

15 Claims, No Drawings

IMMOBILIZATION OF LIPASE FOR RESOLVING RACEMATES OF ESTERS OF RACEMIC ALCOHOLS

The present invention relates to a simple and economical process for the preparation of an immobilizate of crude pancreas lipase, based on a polymer of one or more vinyllactams, the immobilizate itself and its use for resolving racemates of esters of racemic alcohols.

Techniques for immobilizing lipase are known. According to U.S. Pat. No. 4,629,742, lipase obtained from Candida cylindracea is used for immobilization. Hydrophobic polymers, especially polyethylene and polypropylene have proven useful as a substrate for the immobilizate.

The process for immobilization described in EP-A-210 499, inter alia for pancreas lipase, by gel formation from the enzyme, a polyepoxide and a polyamine is simple but gives biocatalysts which have low mechanical stability and poor hydrodynamic properties (filterability, flow resistance in columns packed with the biocatalyst) and are therefore not very suitable for industrial use.

The enantioselective resolution of racemic esters by means of porcine pancreas lipase on the laboratory scale is also known (W. E. Ladner and G. M. Whitesides, J. Amer. Chem. Soc. 106 (1984), 7250-7251). Crude, nonimmobilized lipase was used in this procedure. This process is unsuitable for industrial use; an economical process requires immobilization. Immobilization by conventional methods, for example according to the above-mentioned U.S. Patent, did not give the desired result since the specific activity of the immobilizate was low and decreased far too rapidly in operation.

It is an object of the present invention to prepare immobilizates of crude pancreas lipase in a simple and economical manner, making it possible to carry out a simple, economical process for resolving racemates of esters of optically active alcohols which is suitable for the industrial scale. Important criteria for a suitable biocatalyst are a long life and a high space-time yield.

We have found that this object is achieved by a process as claimed in claims 1 to 9. The biocatalyst is prepared by mixing a pulverulent, insoluble, only slightly swellable copolymer of one or more N-vinyllactams of 4 to 6 carbon atoms, preferably N-vinylpyrrolidone, with from 0.5 to 10 % by weight, based on the total monomers, of a cyclic amide which contains two or more ethylenically unsaturated, copolymerizable groups, one or more of which are bonded directly to amide nitrogen, preferably N,N'-divinylethyleneurea, a lipase and water at pH 5-9, preferably 5.5-8 and at from 0° to 40° C., preferably from 10° to 30° C., and, after from one minute to 3 days, preferably from 1 to 10 hours, filtering the mixture and washing the filter cake with water or buffer solution or a water-soluble organic solvent, wherein the lipase used is commercial porcine pancreas lipase which is crude, ie. contains up to 99 % by weight of natural impurities (especially proteins), and is therefore very readily and economically available, and one or more water-soluble aliphatic alcohols having from 2 to 6 carbon atoms and from 2 to 6 hydroxyl groups, if necessary as a mixture with a monohydric alcohol of 1 to 4 carbon atoms, are added to the aqueous mixture as a stabilizer for the lipase (to prolong its activity).

The preparation of the copolymer of one or more vinyllactams with a cyclic amide which contains two or more ethylenically unsaturated, copolymerizable groups, one or more of which are bonded to amide nitrogen, which copolymer is to be used according to the invention, can be carried out according to U.S. Pat. No. 3,992,562 or U.S. Pat. No. 4,013,825. The polymerization takes place spontaneously, without the conventional initiators, in the absence of air at a pH of from 6 to 9 and at elevated temperatures, either in the presence of a small amount of a sulfur compound in which the sulfur has a valence lower than 6, or in the presence of an $\alpha$- or $\beta$-ketocarboxylic acid. The copolymers are by their very nature porous.

Suitable vinyllactams, which can be copolymerized, alone or as a mixture with one another, with the amides which act as crosslinking agents and contain two or more copolymerizable double bonds, are N-vinylcaprolactam, N-vinylpiperid-2-one and, preferably, N-vinylpyrrolidone.

A preferred cyclic amide having two or more ethylenically unsaturated, copolymerizable double bonds is N,N'-divinylethyleneurea.

The particle size of the copolymer should be from 1 $\mu$m to 1 mm, preferably from 10 to 500 $\mu$m, depending on the particular use. The lower limit is determined by the filterability or the hydrodynamic resistance of a column packed with the said copolymer, and the upper limit is determined by the time taken for the substrate solution to diffuse into the interior of the particles (which in turn depends, inter alia, on the pore size). The pore size is from 2 to 200 nm, preferably from 5 to 100 nm, measured by mercury porosimetry.

Although the lipase itself is water-soluble, many constituents of the crude lipase are water-insoluble and are suspended in the reaction mixture.

Water-soluble solvents and alcohols are those which have a water solubility of not less than 10, preferably not less than 20, % by weight at 20° C. Particularly preferred solvents and alcohols are those which are infinitely miscible with water. The valence of the alcohol is the number of hydroxy groups. Only slightly swellable means a water absorptivity of the magnitude of 1-3 % by weight.

Examples of suitable water-soluble alcohols which can be used to prolong the activity of the lipase are: ethylene glycol, 1,2- and 1,3-propanediol, 1,2-, 1,3-, 1,4- and 2,3-butanediol, 1,2- and 1,3-isobutanediol, 1,2-and 1,5-pentanediol, diethylene glycol, glycerol, erythritol, pentaerythritol, arabitol, xylitol, sorbitol, mannitol and dulcitol and mixtures of these. Polyhydric water-soluble alcohols having from 2 to 6 OH groups, alone or as a mixture with alcohols having various numbers of OH groups, in particular glycerol, and mixtures of glycerol with methanol, ethanol, 2-propanol and 1,5-pentanediol are preferred. Some of these polyhydric alcohols can also be replaced by one or more of the following monohydric alcohols: methanol, ethanol, 1- and 2-propanol, 2-butanol and tert-butanol.

To bring the pH to 5-9, preferably 5.5-8, it is advantageous to use a conventional buffer mixture, for example a mixture of primary and secondary phosphates, borax, a mixture of tris-(hydroxymethyl)-amine and its hydrochloride, and acetate buffer mixtures.

The total mixture has the following composition: from 1 to 50, preferably from 4 to 30, % of the copolymer of N-vinyllactam described, from 1 to 30, preferably from 5 to 25, % of crude porcine pancreas lipase, from 1 to 68, preferably from 20 to 60, % of one or more of the water-soluble, polyhydric alcohols described, where the amount over and above 1%, preferably above 5%, in particular above 10%, can be replaced by a water-soluble, monohydric alcohol of 1 to 4 carbon atoms, from 30 to 97% of water and the pH-regulating additives (which play hardly any role in terms of weight). The percentages are based in each case on the weight of the total mixture.

The components can be mixed in any order; preferably, the crude lipase is suspended in the mixture of water and alcohol and the polymeric substrate is then added.

The mixture is advantageously allowed to stand for from one minute to 3 days, preferably from 1 hour to 1 day, at from 0° to 40° C., preferably from 10° to 30° C., and is preferably kept in motion (eg. stirring, rolling). It is then filtered. The filter cake can be used directly, in the washed or unwashed state, in an aqueous medium, for resolution of esters. Advantageously, however, it is treated, ie. brought into contact, beforehand for from one minute to 2 hours, preferably from 2 minutes to 1 hour, at room temperature (from 10° to 30° C.) with an aqueous or aqueous alcoholic solution of a cross-linking agent to fix the lipase. Examples of suitable crosslinking agents are dialdehydes, in particular glutardialdehyde and glyoxal, and watersoluble glycidyl ethers, prepared according to EP-A 210 499, by an addition reaction of from 1 to 30 equivalents of an epoxide of the formula I

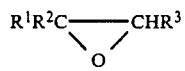 (I)

where $R^1$, $R^2$ and $R^3$ are each hydrogen, methyl or ethyl, with one equivalent (based on OH groups) of a polyfunctional alcohol of 2 to 6 carbon atoms or of a mono- or disaccharide, and reaction of the resulting adduct with one equivalent of epichlorohydrin per OH group, followed by cyclization to give the epoxide.

The immobilizate can be used in a conventional manner, for example in columns or in a stirred reactor.

As a result of the novel process, porcine pancreas lipase has for the first time been converted into a reusable, readily filterable immobilizate which is suitable for use in columns and has a high specific activity and a long useful life. The fact that impurities in the crude lipase do not have an adverse effect makes the process particularly economical.

In the copolymers of N-vinylpyrrolidone and N,N'divinylethyleneurea used for the Examples, pores having a diameter of from 10 to 50 nm were most frequent. The particle size was always less than 500 μm.
Determination of the enzymatic activity of pancreatin In a pH-stat apparatus, 50 ml of borax/HCl buffer (20 mM, pH 7.5) and 1 ml of glycidyl butyrate are mixed with one another and stirred thoroughly at 30° C. A suitable amount (usually 1–10 mg) of crude pancreas lipase or of the immobilizate to be tested (500 mg) is added, after which the pH is kept constant by automatic metering of 0.5 N NaOH solution. The specific enyzmatic Li activity $A_{sp}$ is calculated as follows:

$$A_{sp} = \frac{\Delta V \cdot N}{\Delta t \cdot m}$$

$\Delta V/\Delta t$ is the amount of sodium hydroxide solution consumed at the beginning of the reaction, in ml/min, N is the normality of the sodium hydroxide solution (500 μmol/ml) and m is the amount of enzyme or of immobilizate weighed in.

The usual unit for the enzymatic activity is 1 unit (abbreviated to u), corresponding to a NaOH consumption of 1 μmol/min.

The specific activity of the Nordmark pancreatin used for immobilization was 17 u/mg.

In the Examples, parts and percentages are by weight. Preparation of the immobilizate

EXAMPLE 1

2 g of crude porcine pancreas lipase were suspended in 18 g of a mixture of 80 parts of 200 millimolar phosphate buffer of pH 7.0, 10 parts of glycerol and 10 parts of isopropanol. 1 g of a copolymer prepared according to U.S. Pat. No. 3,992,562 from 100 parts of N-vinylpyrrolidone and 2 parts of N,N'-divinylethyleneurea was added to this suspension.

This mixture remained at room temperature overnight in the absence of air, and 5.4 g of 25% strength aqueous glutardialdehyde solution was added the next day. After one hour, the immobilizate was filtered off under suction and washed with a mixture of 80 parts of 200 millimolar phosphate buffer, 10 parts of glycerol and 10 parts of isopropanol.

2.7 g of immobilizate were obtained. This was used twice for the resolution of esters, the specific enzymatic activity being shown in the Table:

| Batch | $A_{sp}$ [u/g] | $A_{rel.}$ in % |
|---|---|---|
| 1 | 1333 | — |
| 2 | 1282 | 96 |

EXAMPLE 2

1 g of crude porcine pancreas lipase was suspended in 15 g of a mixture of 70 parts of 50 millimolar borate buffer of pH 8.0, 20 parts of glycerol and 10 parts of ethanol. 1 g of a copolymer prepared according to U.S. Pat. No. 3,992,562 from 100 parts of N-vinylpyrrolidone and 2 parts of N,N'-divinylethyleneurea was added to this suspension. This mixture remained overnight at 8° C. in "the absence of air, and 3.0 g of sorbitol-EO$_{80}$ epoxide were added the next day. After one hour, the immobilizate was filtered off under suction and washed with the above mixture of borate buffer, glycerol and ethanol. 2.9 g of immobilizate were obtained. This was used twice for the resolution of esters, the specific activity being shown in the Table:

| Batch | $A_{sp}$ [u/g] | $A_{rel.}$ in % |
|---|---|---|
| 1 | 980 | — |
| 2 | 952 | 97 |

The sorbitol-EO$_{80}$ epoxide had an epoxide value of 1.2 mmol/g and was prepared as follows (DE 35 27 014):

14 8 g of BF$_3$ dihydrate were added to 3705 g of sorbitol-EO$_{80}$ (reaction product of 1 mole of sorbitol with 80 moles of ethylene oxide, cf. Houben-Weyl, Methoden der Org. Chemie 14/2 (1963), page 450). Thereafter, 555 g of epichlorohydrin were added dropwise at 70° C., while stirring. Stirring was continued for a further 2 hours at 70° C., after which 528 g of 50% strength sodium hydroxide solution were added dropwise at from 20° to 35° C. in the course of from 1 to 2 hours. Stirring was continued until about 90% of the sodium hydroxide solution had been consumed. The consumption of sodium hydroxide solution was monitored by titration.

The major part of the water was distilled off at 70° C. under reduced pressure from a water pump, and the residue was filtered off under suction at elevated temperatures (70° C.).

This gave 3,439 g (85%) of a reaction product of epichlorohydrin with sorbitol-$EO_{80}$, which product had an epoxide titer of 1.2 mmol/g.

EXAMPLE 3

2 g of crude porcine pancreas lipase were suspended in 18 g of a mixture of 200 millimolar phosphate buffer of pH 8.0 and an alcohol (cf. Table). 1 g of a copolymer (U.S. Pat. No. 3,992,562) of 100 parts of N-vinylpyrrolidone and 2 parts of N,N'-divinylethyleneurea was added to this suspension. This mixture was rolled overnight in a cylindrical vessel. The laden substrate was filtered off under suction, and a solution which contained 300 mg of aqueous glutardialdehyde solution (25%) per milliliter of the corresponding alcohol/phosphate buffer solution was added. After one hour, the immobilizate was filtered off under suction and washed with the particular alcohol/phosphate buffer solution.

| Alcohol [parts by wt.] | | Phosphate buffer [parts by wt.] | Batch | $A_{sp}$ [u/g] | $A_{rel.}$ in % |
|---|---|---|---|---|---|
| Methanol 10 | Glycerol 20 | 70 | 1 | 950 | — |
| | | | 2 | 903 | 95 |
| 1,5-pentanediol 10 | Glycerol 20 | 70 | 1 | 895 | — |
| | | | 2 | 832 | 93 |
| Isopropanol 10 | Glycerol 20 | 70 | 1 | 1010 | — |
| | | | 2 | 950 | 94 |
| Isopropanol — | Glycerol 30 | 70 | 1 | 540 | — |
| | | | 2 | 490 | 91 |

COMPARATIVE EXPERIMENT

Using A Different Substrate 2 g of crude porcine pancreas lipase were suspended, according to EP-A-210 499, in 8 g of a solution of 50 parts of 50 millimolar phosphate buffer of pH 8.0 and 50 parts of glycerol, and the suspension was mixed with 6.5 g of sorbitol-$EO_{80}$ epoxide (cf. Example 5) and 4.0 g of polyethyleneimine solution (25% strength in water, brought to pH 8.0 with HCL). After 24 hours, the resulting gel was forced through a sieve of 1 mm mesh size.

| Batch | $A_{sp}$ [u/g] | $A_{rel.}$ in % |
|---|---|---|
| 1 | 53 | — |
| 2 | 32 | 60 |
| 3 | 28 | 53 |

The immobilizates were soft and agglomerated during filtration.

COMPARATIVE EXPERIMENT 2

Without The Addition Of Alcohol 2 g of crude porcine pancreas lipase were suspended in 18 g of 200 millimolar phosphate buffer, followed by 1 g of a copolymer prepared according to U.S. Pat. No. 4,013,825 from 100 parts of N-vinylpyrrolidone and 2 parts of N,N'-divinylethyleneurea. The mixture was left to stand overnight, and the product was filtered off under suction on the next day and washed with 200 millimolar phosphate buffer.

The same immobilizate was used twice for the resolution of esters, the specific activities being shown in the Table:

| Batch | $A_{sp}$ [u/g] | $A_{rel.}$ in % |
|---|---|---|
| 1 | 201 | — |
| 2 | 108 | 54 |

COMPARATIVE EXPERIMENT 3

Four other lipases were used, similarly to Example 1:
Lipase Saiken 100 obtained from Rhizopus japonicus, from K. K. Osaka Saihin Kenkyusho
Lipase M-AP 10 obtained from Mucor sp., from Amano Pharmaceutical Co. Ltd.
Piccantase-A obtained from Mucor miehei, from Gist-Brocades
Lipase My obtained from Candida cylindracea, from Meito Sangyo.

The first three had no enzymatic activity in the resolution of esters; the specific activities of the lipase My are shown in the Table:

| Batch | $A_{sp}$ (CB) [u/g] | $A_{rel.}$ in % |
|---|---|---|
| 1 | 205 | — |
| 2 | 165 | 80 |

USE EXAMPLE 1.4 l of a 0.05 M buffer solution ($Na_2B_4O_7.10H_2O$) brought to pH 7 with concentrated hydrochloric acid were cooled to 6° C. 216.1 g (1.5 moles) of racemic glycidyl butyrate and 15 g of moist immobilizate washed with pH 7 buffer solution were added. The mixture was stirred thoroughly at 9°–10° C. and was not kept at about pH 7.3 by pumping in 10N NaOH (a total of 82.5 ml (0.825 mole), corresponding to 55% hydrolysis). After 150 minutes, the stated amount of NaOH had been consumed. The immobilizate was filtered off, washed twice with $CH_2CL_2$ and once with pH 8 buffer and then suspended in pH 7 buffer and stored at 5°–8° C. The filtrate and the wash phases were combined and shaken thoroughly, and the organic phase was separated off. The aqueous phase was extracted three times more with $CH_2CL_2$. The combined organic phases were dried over sodium sulfate and evaporated down in a rotary evaporator under reduced pressure, and the residue was distilled. 73 g of R(−)glycidyl butyrate were obtained (0.5 mole, 75% yield, based on the 0.67 mole of R(−)gylcidyl butyrate theoretically obtainable at 55% hydrolysis). Optical rotation $[\alpha]^D_{20}=29.2°$, bp. 83°C./14 mbar.

We claim:

1. A process for the preparation of an immobilized lipase, which comprises:
   (a) mixing a substrate, crude porcine pancreatic lipase, an aqueous buffer solution at pH 5-9 and one or more water-soluble polyhydric aliphatic alcohols having from 2 to 6 carbon atoms and from 2 to 6 hydroxyl groups at a temperature of from 0° to 40° C., and allowing the mixture to stand for from 1 minute to 3 days, and wherein said substrate is a pulverulent, insoluble, only slightly swellable copolymer of one or more N-vinyllactams of 4 to 6 carbon atoms with a cyclic amide which contains two or more ethylenically unsaturated, copolymerizable groups, one or more of which are bonded directly to amide nitrogen; and
   (b) filtering the mixture to produce a filter cake, and washing the cake, to obtain said immobilized lipase.

2. The process as claimed in claim 1, wherein the N-vinyllactam used in N-vinylpyrrolidone.

3. The process as claimed in claim 1, wherein N,N'-divinylethyleneurea is used as the cyclic amide having two or more ethylenically unsaturated, copolymerixable double bonds.

4. The process as claimed in claim 1, which further comprises treating said filter cake with a crosslinking agent.

5. The process as claimed in claim 4, wherein the crosslinking agent used is glutardialdehyde.

6. The process as claimed in claim 4, wherein the crosslinking agent used is a water-soluble glycidyl ether which is prepared by an addition reaction of from 1 to 30 equivalents of an epoxide of the formula I:

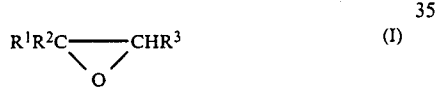

$$R^1R^2C\underset{O}{\overset{}{\diagdown\diagup}}CHR^3 \qquad (I)$$

where $R^1$, $R^2$ and $R^3$ are each hydrogen, methyl or ethyl, with one equivalent, based on HO groups, of a polyfunctional alcohol of 2 to 6 carbon atoms or of a mono- or disaccharide, whereby an adduct is formed, and reacting said adduct with one mole of epichlorohydrin per equivalent of OH, followed by cyclization to give the epoxide.

7. The process as claimed in claim 1, wherein said vinyllactam is selected from the group consisting of N-vinylcaprolactam, N-vinylpiperide-2-one and N-vinylpyrrolidone.

8. The process as claimed in claim 1, wherein said copolymer has a particle size of from 1 μm to 1 mm and a pore size of from 2 to 200 mm.

9. The process as claimed in claim 1, wherein said one or more water-soluble polyhydric aliphatic alcohols have further added thereto one or more water-soluble monohydric alcohols having from 1 to 4 carbon atoms.

10. The process as claimed in claim 9, wherein said polyhydric aliphatic alcohol is glycerol or 1,5-pentanediol or a mixture thereof, and said monohydric alcohol is selected from the group consisting of methanol, ethanol and isopropanol.

11. The process as claimed in claim 1, wherein the mixture contains from 1 to 50% of the copolymer of N-vinyllactam, from 1 to 30% of the crude porcine pancreatic lipase and from 1 to 68% of said one or more water-soluble polyhydric aliphatic alcohols, said mixture further containing pH-regulating additives.

12. The process as claimed in claim 11, wherein above 10% of said one or more water-soluble polyhydric aliphatic alcohols are replaced with said one or more water-soluble monohydric alcohols.

13. An immobilized lipase prepared by the process of claim 1.

14. A process for resolving a racemate of an ester of a racemic alcohol in an aqueous medium, which comprises:
   (a) preparing an immobilized lipase by: mixing a substrate, a crude porcine pancreatic lipase, an aqueous buffer solution at pH 5-9 and one or more water-soluble polyhydric aliphatic alcohols having from 2 to 6 carbon atoms and from 2 to 6 hydroxyl groups at a temperature of from 0° to 40° C., and allowing the mixture to stand from 1 minute to 3 days, and wherein said substrate is a pulverulent, insoluble, and only slightly swellable copolymer of one or more N-vinyllactams of 4 to 6 carbon atoms with a cyclic amide which contains two or more ethylenically unsaturated copolymerizable groups, one or more of which are bonded directly to amide nitrogen and filtering the mixture to produce a filter cake, and washing the cake, to obtain the immoblized lipase;
   (b) mixing said racemate with said immobilized lipase; and
   (c) isolating resolved racemate from the immobilized lipase.

15. The process as claimed in claim 14, wherein said racemate is a racemate of glycidyl butyrate.